(12) United States Patent
Goldberg et al.

(10) Patent No.: US 8,491,937 B2
(45) Date of Patent: Jul. 23, 2013

(54) STABILITY IN VITAMIN AND MINERAL SUPPLEMENTS

(75) Inventors: Alan M. Goldberg, Nutley, NJ (US);
Steven Dills, Ashland, VA (US);
William Mark, Morgantown, WV (US);
Bruce Sutton, Richmond, VA (US);
Chad Byerley, Midlothian, VA (US)

(73) Assignee: Wyeth LLC, Madison, NJ (US)

( * ) Notice: Subject to any disclaimer, the term of this patent is extended or adjusted under 35 U.S.C. 154(b) by 606 days.

(21) Appl. No.: 11/706,923

(22) Filed: Feb. 15, 2007

(65) Prior Publication Data

US 2008/0199534 A1    Aug. 21, 2008

(51) Int. Cl.
*A01N 59/26* (2006.01)

(52) U.S. Cl.
USPC ............ 424/602; 514/458; 514/474; 562/569

(58) Field of Classification Search
USPC ................... 424/602; 514/458, 474; 562/569
See application file for complete search history.

(56) References Cited

U.S. PATENT DOCUMENTS

| | | | | |
|---|---|---|---|---|
| 4,647,450 | A | * | 3/1987 | Peters et al. ............... 424/48 |
| 5,670,344 | A | * | 9/1997 | Mehansho et al. ............ 426/74 |
| 6,039,978 | A | | 3/2000 | Bangs et al. |
| 6,361,800 | B1 | | 3/2002 | Cooper et al. |
| 6,440,450 | B1 | | 8/2002 | Han et al. |
| 2003/0138484 | A1 | * | 7/2003 | Gianesello et al. ........... 424/465 |

FOREIGN PATENT DOCUMENTS

| | | |
|---|---|---|
| DE | 94 12 374 U1 | 9/1994 |
| EP | 0 891 776 A | 1/1999 |
| WO | WO 03/043608 | 5/2003 |
| WO | WO 2005/117838 A | 12/2005 |

OTHER PUBLICATIONS

A Study of the Chemical and Physical Stability of Ascorbic Acid, Folic Adic, and Thiamine Hydrochloride Tablets Formulated With Emcompress Standard; "Drug Development Communications". 1(6), 495-505 (1974-1975).

* cited by examiner

*Primary Examiner* — Ali Soroush
(74) *Attorney, Agent, or Firm* — Maureen P. O'Brien; Jeffrey Gold; Stephanie Monaco

(57) ABSTRACT

The invention provides a multivitamin and mineral nutritional supplement composition comprising at least one polyvalent metal and at least one oxidizable vitamin with substantially improved resistance to reactions that lead to darkening and/or spotting and reactions that may reduce the potency of oxidizable vitamins. The composition is a multivitamin and mineral composition comprising at least one polyvalent metal and at least one oxidizable vitamin wherein the composition is substantially free of mobile bound water. The invention also includes methods for making such a composition and methods of preventing or reducing oxidation, improving the stability of oxidizable vitamins, and stabilizing the disintegration time of a multi-vitamin and mineral nutritional supplement composition.

6 Claims, No Drawings

STABILITY IN VITAMIN AND MINERAL SUPPLEMENTS

FIELD OF INVENTION

This invention relates to nutritional supplement compositions. More particularly this invention provides a composition and method to reduce the degradation in vitamin and mineral supplements associated with darkening and/or spotting of multi-component nutritional supplement tablets over time.

BACKGROUND OF THE INVENTION

It has long been established that a number of chemical compounds typically referred to as vitamins and minerals provide significant value to maintaining an individual in a healthy state and/or treating specific medical conditions even when supplied in relatively small amounts. The human body cannot synthesize most of the vitamins and minerals that are essential to maintaining the health of the human body. Thus, vitamins and minerals must be obtained from an external source. The two most common external sources are foods and nutritional supplements. As most people do not eat foods that consistently provide the necessary daily requirements of vitamins and minerals, vitamin and mineral nutritional supplementation has become a recognized method of meeting accepted medical and health standards.

Vitamin and mineral preparations may be administered to treat specific medical conditions or as general nutritional supplements. As there are a number of vitamins and minerals needed and the daily amounts needed are relatively small, it is convenient to administer mixtures of vitamins and minerals in tablet or capsule form as a general supplement. Typical daily dosages of commercially available multivitamin and mineral supplements are one or two tablets or capsules per day. It is not unusual for such compositions to include two dozen or more nutrients in addition to the excipients needed to make the dosage form.

Accordingly, it is not surprising that undesirable chemical interactions can occur in these complex mixtures. The most common of these reactions are degradation reactions that lead to a reduced potency of the impacted nutrients and may also cause the composition to darken or develop unsightly dark spots. Oxidation reactions are exemplary of a common form of degradation reactions. The presence of water may also contribute to degradation either directly or by facilitating reactions such as oxidation reactions, for example.

Both water and fat-soluble vitamin components such as ascorbic acid (vitamin C) and alpha tocopheryl acetate (vitamin E), for example, have been found to be susceptible to moisture induced chemical degradation in multi component supplement compositions. Ascorbic acid oxidation, promoted by the interaction of ascorbic acid with polyvalent metal ions in a dietary supplement composition and facilitated in the presence of water, can cause tablet darkening and/or spotting and prolonged disintegration times that may impact availability of components for utilization in the body.

Conventionally, it has been believed that the water that contributes to degradation, is water in the environment proximate the composition (e.g. environmental water) and/or water that is loosely associated with the surface or interfacial areas of the composition. For example, the commercially available nutritional supplementation product, One-A-Day® Active, includes a storage statement which reads, "If excess moisture enters the bottle, the iron may cause spotting on the tablet."

Accordingly, desiccants have been employed to improve stability. However, there are several problems with desiccants: First, desiccants can be physically removed from a package by the consumer negating the beneficial effect. Secondly, a desiccant may lose efficacy over time and/or have limitations in its ability to remove bound water. Thirdly, desiccants add expense to the final product.

Limiting the contents of tablets to exposure to environmental water by employing tablet coating has also been used. While this method may mask problems from a consumer's view, the polymeric film coatings used to date do not appreciably reduce spotting and/or darkening problems. Examination of aged coated tablets often reveals spotting or core darkening under the coating Shah et al. in "A Study of the Chemical and Physical Stability of Ascorbic Acid, Folic Acid, and Thiamine Hydrochloride Tablets Formulated With Emcompress Standard®" reported that Emcompress Standard® (directly compressible dicalcium phosphate dihydrate granulation) induced ascorbic acid chemical degradation and physical degradation (with regard to disintegration times) in ascorbic acid and thiamine hydrochloride tablets. (Shah, D. H. & Aramblo, A., 1975, *Drug Devel. & Ind. Pharm.*, 1, 459-505) The reference attributed these instabilities to the moisture associated with environmental water or water that is loosely associated with the surface or interfacial areas of the composition.

Accordingly as moisture promoted degradation reactions lead to a loss of potency and/or unappealing discoloration of multi-component nutritional supplements containing mineral ions and oxidizable vitamins, a composition and/or methods are needed to reduce moisture promoted degradation in multi-component nutritional supplements.

SUMMARY OF THE INVENTION

The present invention provides a pharmaceutical composition comprising a multivitamin and mineral composition comprising at least one polyvalent metal and at least one oxidizable vitamin wherein the composition is substantially free of mobile bound water. In an exemplary embodiment the at least one polyvalent metal is selected from the group consisting of iron, magnesium, zinc, selenium, copper, cobalt, manganese, molybdenum, vanadium, nickel, tin and chromium and combinations thereof, and the oxidizable vitamin is selected from the group consisting of Vitamin C, Vitamin E, Vitamin A, Vitamin A precursors, Vitamin $B_6$, Vitamin $D_3$, Vitamin K, Folic Acid and combinations thereof.

In a preferred embodiment, the composition further comprises anhydrous dicalcium phosphate and is in a tablet dosage form.

A method for preparing a multivitamin and mineral composition of the invention is provided. The method comprises providing at least one oxidizable vitamin, at least one polyvalent metal ion and anhydrous dicalcium phosphate; and combining the at least one polyvalent mineral ion, the at least one oxidizable vitamin and anhydrous dicalcium phosphate to form a composition, wherein the composition is substantially free of mobile bound water.

A method for reducing oxidation induced spotting in a multivitamin and mineral composition supplement tablet is provided. The method comprises combining at least one polyvalent metal selected from the group consisting of iron, magnesium, zinc, selenium, copper, cobalt, manganese, molybdenum, vanadium, nickel, tin and chromium and combinations thereof, and at least one oxidizable vitamin selected from the group consisting of Vitamin C, Vitamin E, Vitamin A, Vitamin A precursors, Vitamin $B_6$, Vitamin $D_3$, Vitamin K, folic acid and combinations thereof to form a composition wherein the composition is substantially free of mobile bound water.

DETAILED DESCRIPTION OF THE INVENTION

The invention provides a nutritional supplement composition comprising at least one polyvalent metal and at least one oxidizable vitamin with substantially improved resistance to reactions that lead to darkening and/or spotting and reactions that may reduce the potency of oxidizable vitamins. The invention also includes methods for making such a composition and methods of preventing or reducing oxidation, improving the stability of oxidizable vitamins, and stabilizing the disintegration time of a multi-vitamin and mineral nutritional supplement composition.

The inventors believe without wishing to be held to the theory that minimization of bound water traditionally believed to be unavailable for participation in chemical reactions at ambient or near ambient conditions is important to minimization of spotting and/or darkening of multi-vitamin and mineral compositions comprising polyvalent metal ions and an oxidizable vitamin.

In a preferred embodiment, the composition comprises vitamin C and a polyvalent metal ion, and anhydrous dicalcium phosphate wherein the composition is substantially free of mobile bound water. The invention is directed to solving a problem in conventional commercial multivitamin and mineral tablets which to the observer appear to be dry and which are prepared from well characterized vitamins, minerals and related substances.

In addition to improved chemical stability, the composition of the invention typically has improved consistency of tablet disintegration times over time and is resistant to darkening and/or spotting of the tablet over time frames consistent with commercial product shelf life.

Polyvalent metal cations are believed to serve as catalysts for oxidation of vitamins and the process appears to be facilitated by the presence of water. Traditionally, environmental water or loosely associated surface or interstitial water have been believed to be the source of water that facilitates the oxidation of vitamins in the presence of polyvalent metal ions. An observation supported by the fact that vitamin oxidation is accelerated by increasing humidity, and to a lesser extent by increasing temperature. However, while this source of water can be a factor, spotting can still occur when these sources provide negligible amounts of water.

Certainly, preventing multi-vitamin and mineral supplement tablets having a plurality of vitamins and minerals from being exposed to moisture will help maintain both chemical and physical stability, but it is frequently insufficient to prevent spotting over the commercial shelf life of multi-vitamin and mineral supplements and/or make a significant impact on the lengthening of disintegration times over a time. The inventors have discovered that water of hydration of a crystalline structure traditionally believed to be unavailable for reaction at ambient or near ambient conditions, may play a role in the vitamin oxidation reactions in the presence of polyvalent metal cations that lead to spotting of multi-vitamin and mineral supplement tablets. The present invention provides for minimization of internal bound water available for reaction in a solid dosage form, e.g. mobile bound water. In one exemplary embodiment the propensity for ascorbic acid (e.g. Vitamin C) to interact with polyvalent metal cations is minimized by using anhydrous dicalcium phosphate as a mineral/excipient (e.g., as a source of calcium and phosphorus and as a diluent and/or binder) and avoiding using calcium salts having water of hydration.

As used herein, the term "degradation" means the change of a given chemical species to a different chemical species (e.g. chemical change). Chemical changes which produce spotting and/or decrease the potency of a component or compound or both are of particular interest in relation to this invention.

As used herein, the phrase "disintegration time" means the amount of time it takes for a tablet dosage unit of a nutritional supplement to disintegrate under controlled laboratory conditions. One of ordinary skill in the art is familiar with methods and procedures for determination of disintegration times.

As used herein, the term "stability" may refer to chemical stability and/or physical stability. As used herein, the phrase "chemical stability" means the ability of a compound to maintain its chemical identity over time. Accordingly, stability implies the ability of a chemical species to resist oxidation or other degradation, for example. As used herein, the phrase "physical stability" means the ability of a composition to maintain consistent physical properties over time. The ability of a composition to maintain a consistent disintegration time over time is exemplary of physical stability.

As used herein, the phrase "mobile bound water" means bound water which is attached to a chemical entity via some form of bonding and that may become available to facilitate chemical reactions under ambient or near ambient conditions. Water of hydration, particularly water of hydration in the crystalline structure of dicalcium phosphate dihydrate is exemplary. Although generally considered to be bound and stable under ambient or near ambient conditions (e.g. typical conditions of shipping, storage and use), in the presence of oxidizable vitamins and polyvalent metal ions the water bound as water of hydration can facilitate the oxidation reaction. As used herein the term "substantially free of mobile bound water" means less than 0.3% by weight of the composition can be attributed to water of hydration or other formally bound water that may become available for reaction under ambient or near ambient conditions. Accordingly, the use of a component that has mobile bound water is preferably avoided, but substantially free of mobile bound water recognizes that very small amounts of water of hydration associated with nutrients may be used and/or that trace amounts of hydrated forms may be present in compositions designated as anhydrous.

The term "multivitamin and mineral" or "multivitamin and multimineral" supplement(s) should be interpreted to mean conventional commercial type vitamin and mineral supplements prepared from specific vitamin and mineral materials. Multivitamin and mineral supplement includes compositions comprising, at least one vitamin and at least one mineral and, optionally, related nutritional agents such as carotinoids. However, as used herein the term multivitamin and mineral supplement does not include supplements with complex plant extracts such as for example complex multi-component herbal extracts and/or compositions with large amounts of hydrophobic material (e.g. greater than 30% highly hydrophobic material such as, for example, phytosterols) which add additional complexities to the supplement composition. In other words the invention is directed to resolving a problem associated with conventional mass produced nutritional supplements generally referred to as multivitamin and mineral supplements that containing a plurality of vitamins and a plurality of minerals. The terms "multivitamin and mineral" or "multivitamin and multimineral" should be interpreted in an equivalent manner herein when they proceed the terms "nutritional supplement", "tablet", or "composition".

The term "potency" relates to the amount of efficacious component. Typically, as used herein, it refers to the efficacious amount of a given component at a given time in comparison to the efficacious amount of the same component at a second time. Typically, potency is expressed as a percentage. For example, a 20% reduction in potency of component A after three months means that the efficacious amount of component A present after a three month period is 80% of the original efficacious amount of component A.

As used herein, the term "polyvalent metal" means a metal ion having a valence of 2 or higher.

As used herein, the term "oxidizable vitamin" may apply to either a fat or water soluble vitamin that is subject to oxidative degradation, and whose oxidation may be facilitated by the presence of water and a polyvalent metal. Oxidizable vitamins include, but are not limited to, Vitamin C, Vitamin E, Vitamin A, Vitamin A precursors, Vitamin $B_6$, Vitamin $D_3$, Vitamin K, and folic acid.

As discussed above, the invention addresses the undesirable interaction of oxidizable vitamins with polyvalent metal ions in the presence of mobile bound water. Accordingly, the invention is applicable to a solid form composition containing one oxidizable vitamin and one polyvalent metal ion whether the oxidizable vitamin and the polyvalent mineral ion are the sole active agents or part of a mixture of vitamins and minerals. As noted above, the invention is particularly directed to complex mixtures of vitamins and minerals of the type found in commercial multi-vitamin and mineral supplements. A listing of vitamins and minerals and related agents that may be included in nutritional supplements and dosage amounts are set forth in established reference guides such as the United States Pharmacopeia National Formulary Official Compendium of Standards (i.e., the U.S.P.-N.F. Official Compendium of Standards) or European Directive 90/496/EC including amendments which are incorporated herein by reference. Amounts of vitamins and minerals may vary in specific embodiments but should typically fall within the dosage amounts set forth in the U.S.P.-N.F. Official Compendium of Standards or European Union Directive.

Vitamins and related entities which may be included in multivitamin and mineral preparations include but are not limited to Vitamin C, Vitamin, E, thiamin (Vitamin B1), riboflavin (Vitamin $B_2$), niacin (Vitamin $B_3$), pyridoxine (Vitamin $B_6$), folic acid, cobalamins (Vitamin $B_{12}$), Pantothenic acid (Vitamin $B_5$), Biotin, Vitamin A (and Vitamin A precursors), Vitamin D, Vitamin K, other B complex vitamins, B complex related compounds such as Choline and Inositol, for example, and carotinoids such as lutein, lycopene, zeaxanthin, and astaxanthin. Of these vitamins, Vitamin C, Vitamin E, Vitamin A, Vitamin $B_6$, Vitamin $D_3$, Vitamin K and folic acid are know to be susceptible to oxidation in multivitamin and mineral preparations. Any vitamin susceptible to oxidation in the presence of a polyvalent cation at ambient conditions is within the scope of the invention; however, of the vitamins listed above, Vitamin C and vitamin E are particularly susceptible to oxidation in the presence of polyvalent metal ions.

Vitamin C is commonly provided as ascorbic acid in multivitamin-multimineral tablets. As ascorbic acid is particularly susceptible to oxidation, it commonly is a significant contributor to spotting and darkening. Alternatively, ascorbyl palmitate, a hydrophobic ester of Vitamin C which has a reduced affinity for water may be used. Reduced spotting is observed using acorbyl palmitate, but use of ascorbyl palmitate has disadvantages which need to be carefully considered. Ascorbyl palmitate is relatively expensive compared to ascorbic acid and is less potent than ascorbic acid (42.5% vitamin C potency) necessitating higher use levels and larger tablets for consumers to swallow. Ascorbyl palmitate also has poor powder flow properties which lead to processing problems particularly during compression and typically yields tablets that are subject to substantial increases of disintegration times over product shelf life time frames.

Coating or encapsulating ascorbic acid with various barrier coatings is a possible alternative to preventing or slowing oxidation. The inventors explored this strategy, but for the experiments conducted found polymeric film coating to have an undesirable negative impact on tablet disintegration. Accordingly, the inventors' discovery that water of hydration can facilitate oxidation of Vitamin C and that avoiding including components having mobile bound water in compositions comprising Vitamin C, provides a practical, cost effective means for reducing degradation reactions that lead to darkening or spotting.

Vitamin E is typically provided as DI-alpha tocopheryl acetate in multivitamin- and mineral tablets. Like Vitamin C, Vitamin E has been found to be particularly susceptible to moisture induced chemical degradation in the presence of polyvalent metal ions. Typically, Vitamin E oxidation does not contribute significantly to spotting, but the oxidation of Vitamin E leads to marked decreases in its potency over time. Accordingly, the oxidation of Vitamin E can impact the quality of the nutritional supplement over time. Likewise, avoidance of including components having mobile bound water in compositions comprising Vitamin E reduces oxidation of Vitamin E.

Minerals which may be included in multivitamin and mineral supplements include, but are not limited to, iron, iodine, magnesium, zinc, selenium, copper, calcium, manganese, silicon, molybdenum, vanadium, boron, nickel, tin phosphorus, chromium, cobalt, chloride, and potassium. Mineral components of multivitamin-multimineral tablets are typically provided in salt form. The salt form used should be a pharmaceutically acceptable salt form.

In some cases the salts may be hydrated forms having bound water of crystallization. For some hydrated salts such as, for example, dicalcium phosphate dihydrate, the bound water of crystallization is mobile bound water that can become available to facilitate oxidation reactions at ambient or near ambient conditions. Accordingly, avoiding use of salt forms that contain mobile bound water removes a significant source of water and reduces the propensity for moisture facilitated oxidation reactions to occur. Using anhydrous dicalcium phosphate as a calcium source/excipient instead of the commonly used dicalcium phosphate dihydrate is exemplary. Salts with water of hydration may be generally avoided, or as water of hydration in crystalline structures has traditionally been considered to be unavailable under ambient conditions, testing to determine if a hydrated salt can contribute to the oxidation process may be done. Such testing could be accomplished in any of several ways. For example, a test composition comprising the hydrated salt, an oxidizable vitamin and a polyvalent metal ion could be prepared and subjected to stability testing.

Many minerals salts comprise polyvalent metal ions. For example, typically iron, magnesium, zinc, selenium, copper, cobalt, manganese, molybdenum, vanadium, nickel, tin and chromium are provided in a salt form in which the metal is in a polyvalent state. Any polyvalent metal ion may catalyze oxidation reactions; however, iron and copper ions are known to be particularly problematic in multivitamin and mineral compositions.

While water of hydration associated with any salt used in a multivitamin and mineral composition may potentially be a source of mobile bound water, the inventors have identified commonly used hydrated calcium salts to be particularly problematic. Dicalcium phosphate, dihydrate is commonly used in commercial multivitamin and mineral preparations because it is a low cost ingredient that provides several benefits. In addition to providing calcium and phosphorus nutrients, it is a useful excipient for preparing tablets serving as a binder and/or diluent. Due to its excipent/nutrient role, dicalcium phosphate often comprises a significant amount of a commercial multivitamin and mineral tablet.

Accordingly, for at least the reason of amount used, eliminating the use of the common hydrated form of dicalcium phosphate can reduce a significant amount of the mobile bound water available to facilitate the undesirable oxidation reactions. In one embodiment, elimination of the mobile bound water associated with dicalcium phosphate is accomplished by using anhydrous dicalcium phosphate. Anhydrous dicalcium phosphate provides the calcium and phosphorus nutrient benefits and excipient benefits without any mobile bound water to contribute to the undesirable oxidation reactions. While use of anhydrous dicalcium phosphate is generally beneficial, it is particularly beneficial in compositions comprising large amounts of calcium (e.g. compositions comprising more than 150 mg of elemental calcium per tablet). Further, anhydrous dicalcium phosphate may be used as the sole source of elemental calcium in the multi-vitamin and mineral composition or, alternatively, used in combination with other calcium sources such as, for example, calcium carbonate.

The multi-vitamin and mineral nutritional compositions in accordance with the present invention are intended for oral administration in a solid form. Accordingly, in order to form a solid dosage form, the composition may further comprise excipients and/or processing aides in addition to vitamins and minerals. Exemplary excipients and processing aids, include but are not limited to, absorbents, diluents, flavorants, colorants, stabilizers, fillers, binders, disintegrants, lubricants, wetting agents, glidants, antiadherents, sugar or film coating agents, preservatives, buffers, artificial sweeteners, natural sweeteners, dispersants, thickeners, solubilizing agents and the like or some combination thereof.

Generally, excipients and processing aids known to those skilled in the art are suitable for use in multivitamin and mineral compositions of the invention so long as they do not include water that can facilitate oxidation reactions. For example, in some embodiments containing ascorbic acid it may be desirable to avoid using starch as an excipient for granulating ascorbic acid as starch is hygroscopic. An exemplary suitable granulating agent for ascorbic acid is HPMC (hydroxypropylmethylcellulose)

The dosage form of the compositions of the present invention is a solid. However, solid dosage form may contain non-aqueous liquid or semi-solid components. Exemplary solid dosage forms includes, but are not limited to, tablets, caplets, capsules, chewable dosage forms, powder, sachet and the like. The daily dosage may be included in a single delivery unit or may comprise multiple delivery units. Dividing the daily dosage among multiple delivery units may be desirable if a tablet is used, for example, to provide a tablet size that is convenient to swallow. If multiple delivery units are used, they may be administered one at a time or administered at intervals during the dosage period (e.g. typically a day) if desired. Accordingly, it should be understood that any amounts of the vitamins, minerals or other related nutritional agent disclosed herein are for a daily dosage and that dosage may be delivered in a single delivery unit or multiple delivery units. Further, dosages are for the amount of the specified species of nutrient and the mass of any counter ion and/or ligand associated with the specified species is not included in the specified amount.

In a preferred embodiment, the multivitamin and mineral supplement is a tablet prepared by a direct compression method avoiding exposing the composition to liquid water in the manufacturing process. The ingredients of the composition can be preblended, sequentially combined, or combined through other dry granulation methods. Alternatively, wet granulation may be used. However, if wet granulation and/or aqueous based coating is used processing steps should be designed to limit exposure to water in processing and provide effective drying upon completion of granulation and/or coating.

Example 1

Three examples of the composition of exemplary embodiments of the invention are provided in Tables 1, 2, and 3. These compositions are representative and examples of the many compositions that are within the scope of the invention and are provided for illustrative purposes. The multi-vitamin and mineral nutritional supplements exemplified in Tables 1-3 are intended to be a daily dosage and typically would be administered in one or more dosage units (e.g. one or more tablets). If multiple dosage units are used they may be taken at one time or spaced intervals during the day. The amounts indicated are of the specified nutrient component and do not include the mass of any counter ions. Accordingly, the specified component may be derived from any pharmaceutically acceptable compound or salt. Further the examples give amounts of nutrients (e.g. vitamins or minerals) and it should be understood that the specified nutrients may be combined with one or more excipients to prepare a final dosage form.

TABLE 1

| Ingredient | Amount/Daily Dosage |
| --- | --- |
| Vitamin A (and precursors) | 3500 IU |
| Vitamin D | 400 IU |
| Vitamin E | 30 IU |
| Vitamin C (ascorbic acid) | 60 mg |
| Vitamin B1 (thiamin) | 1.5 mg |
| Vitamin B2 (riboflavin) | 1.7 mg |
| Niacin | 20 mg |
| Vitamin B6 (pyridoxine) | 2 mg |
| Folic Acid | 400 mcg |
| Vitamin B12 (cyanocobalamin) | 6 mcg |
| Pathothenic Acid | 10 mg |
| Calcium | 220 mg |
| Phosphorus | 110 mg |
| Magnesium | 50 mg |
| Copper | 1 mg |
| Iron | 18 mg |
| Manganese | 2 mg |
| Zinc | 15 mg |

TABLE 2

| Ingredient | Amount/Daily Dosage |
| --- | --- |
| Vitamin A (and precursors) | 3000 IU |
| Vitamin D | 400 IU |
| Vitamin E | 45 IU |
| Vitamin K | 50 mcg |
| Vitamin C (ascorbic acid) | 90 mg |
| Vitamin B1 (thiamin) | 1.5 mg |
| Vitamin B2 (riboflavin) | 1.7 mg |
| Niacin | 20 mg |
| Vitamin B6 (pyridoxine) | 2 mg |

TABLE 2-continued

| Ingredient | Amount/Daily Dosage |
|---|---|
| Folic Acid | 400 mcg |
| Vitamin B12 (cyanocobalamin) | 6 mcg |
| Pathothenic Acid | 10 mg |
| Biotin | 30 mg |
| Calcium | 200 mg |
| Phosphorus | 100 mg |
| Magnesium | 100 mg |
| Potassium | 40 mg |
| Boron | 150 mcg |
| Chromium | 120 mcg |
| Copper | 2 mg |
| Iodine | 150 mcg |
| Iron | 18 mg |
| Manganese | 2 mg |
| Molybdenum | 25 mcg |
| Selenium | 25 mcg |
| Silicon | 2 mg |
| Tin | 10 mcg |
| Vanadium | 10 mcg |
| Zinc | 15 mg |
| Nickel | 5 mcg |
| Chloride | 36 mg |
| Lutein | 300 mcg |
| Lycopene | 600 mcg |
| Astaxanthin | 100 mcg |
| Zeaxanthin | 300 mcg |
| Inositol | 50 mg |
| Choline | 55 mg |

TABLE 3

| Ingredient | Amount/Daily Dosage |
|---|---|
| Vitamin A (and precursors) | 5000 IU |
| Vitamin D | 200 IU |
| Vitamin E | 60 IU |
| Vitamin K | 25 mcg |
| Vitamin C (ascorbic acid) | 120 mg |
| Vitamin B1 (thiamin) | 4.5 mg |
| Vitamin B2 (riboflavin) | 5.1 mg |
| Niacin | 40 mg |
| Vitamin B6 (pyridoxine) | 6 mg |
| Folic Acid | 800 mcg |
| Vitamin B12 (cyanocobalamin) | 18 mcg |
| Pathothenic Acid | 20 mg |
| Biotin | 45 mcg |
| Calcium | 250 mg |
| Phosphorus | 160 mg |
| Magnesium | 40 mg |
| Potassium | 80 mg |
| Boron | 60 mcg |
| Chromium | 120 mcg |
| Copper | 0.5 mg |
| Iodine | 150 mcg |
| Iron | 9 mg |
| Manganese | 4 mg |
| Molybdenum | 75 mcg |
| Selenium | 70 mcg |
| Silicon | 4 mg |
| Zinc | 7.5 mg |
| Chloride | 72 mg |

Example 2

Table 4 shows stability data for tablets of an exemplary embodiment of the invention prepared with anhydrous dicalcium phosphate as compared to the same combination of ingredients prepared in the same manner with the exception that dicalcium phosphate dihydrate was used instead of anhydrous dicalcium phosphate. Both sets of tablets comprised 60 mg/tablet Ascorbic Acid (Vitamin C) and 30 IU/tablet Vitamin E and the polyvalent metal cations of 18 mg/tablet Iron (as ferrous fumarate), 100 mg/tablet Magnesium (as magnesium oxide), 2 mg/tablet copper (as cupric oxide), 15 mg/tablet zinc (as zinc oxide), 2.5 mg/tablet manganese (as manganese sulfate) 5 mcg/tab Nickel (as nickel sulfate) and 25 mcg/tablet Chromium (as chromium chloride). As indicated above, the only distinction between the two sets of tablets was that one batch was prepared using dicalcium phosphate dihydrate and the other batch was prepared using anhydrous dicalcium phosphate. In both batches the amount of calcium per tablet was 162 mg and the amount of phosphorus per tablet was 125 mg. The tablets were stored under the stressed conditions of 1 week at 55 C/95% Relative Humidity ("RH") plus 3 months at 40 C/75% RH. The tablets were examined and tested initially and at the end of the test period.

TABLE 4

| | Vitamin C Stability % of initial amount | Vitamin E Stability % of initial amount | Disintegration Time (Initial) | Disintegration Time (After) |
|---|---|---|---|---|
| dicalcium phosphate dihydrate | 57.4 | 62.5 | 2.9–3.9 mins | More than 1 hr |
| anthydrous dicalcium phosphate | 90.8 | 94.2 | 2.9–3.4 mins | 8.5–10.2 mins |

As Table 4 shows, under the specified stress conditions, tablets prepared with anhydrous dicalcium phosphate showed a substantially higher potency of Vitamins C and E at the end of the time period than those prepared with dicalcium phosphate dihydrate (e.g. for Vitamin C 90.8% as compared to 57.4% and for Vitamin E 94.2% as compared to 62.5%). Also the disintegration times for the tablets prepared with the anhydrous dicalcium phosphate showed substantially less change over time than the disintegration times for the tablets prepared using dicalcium phosphate dihydrate.

Upon visual examination at the end of three month period, the tablets prepared with anhydrous dicalcium phosphate showed no evidence of spotting and the tablets prepared with dicalcium phosphate dihydrate had substantial internal and external spotting.

Although the foregoing invention has been described in some detail by way of illustration and examples for purposes of clarity of understanding it will be obvious that certain changes and modifications may be practiced within the scope of the appended claims. Modification of the above-described modes of practicing the invention that are obvious to persons of skill in the art are intended to be included within the scope of the following claims.

What is claimed is:

1. A multivitamin and mineral composition comprising (a) at least one polyvalent metal selected from the group consisting of iron, magnesium, zinc, selenium, copper, cobalt, manganese, molybdenum, vanadium, nickel, tin, chromium and combinations thereof and (b) at least one oxidizable vitamin selected from the group consisting of Vitamin C, Vitamin E, Vitamin A, Vitamin A precursors, Vitamin $B_6$, Vitamin $D_3$, Vitamin K, folic acid and combinations thereof, and (c) anhydrous dicalcium phosphate, and (d) niacin and (e) pantothenic acid; wherein (i) the composition is substantially free of mobile bound water; (ii) the composition does not contain a hydrate form of any ingredient contained therein; (iii) the composition resists reactions that reduce the potency of oxidizable vitamins; (iv) the composition reduces oxidation induced spotting of the tablet; and (v) the composition stabilizes disintegration behavior of the tablet.

2. The multivitamin and mineral composition of claim 1, further comprising a carotinoid.

3. A method for preparing a multivitamin and mineral composition comprising: providing (a) at least one oxidizable vitamin selected from the group consisting of Vitamin C, Vitamin E, Vitamin A, Vitamin A precursors, Vitamin $B_6$, Vitamin $D_3$, Vitamin K, folic acid and combinations thereof and (b) at least one polyvalent metal ion selected from the group consisting of iron, magnesium, zinc, selenium, copper, cobalt, manganese, molybdenum, vanadium, nickel, tin, chromium and combinations thereof and (c) anhydrous dicalcium phosphate; (d) niacin and (e) pantothenic acid; and combining the at least one polyvalent mineral ion, the at least one oxidizable vitamin and anhydrous dicalcium phosphate to form a composition wherein (i) the composition is substantially free of mobile bound water; (ii) the composition does not contain a hydrate form of any ingredient contained therein; (iii) the composition resists reactions that reduce the potency of oxidizable vitamins; (iv) the composition reduces oxidation induced spotting of the tablet; and (v) the composition stabilizes disintegration behavior of the tablet.

4. A method for preparing a multivitamin and mineral tablet comprising: combining (a) at least one polyvalent metal selected from the group consisting of iron, magnesium, zinc, selenium, copper, cobalt, manganese, molybdenum, vanadium, nickel, tin, chromium and combinations thereof, and (b) at least one oxidizable vitamin selected from the group consisting of Vitamin C, Vitamin E, Vitamin A, Vitamin A precursors, Vitamin $B_6$, Vitamin $D_3$, folic acid and combinations thereof and (c) anhydrous dicalcium phosphate (d) niacin and (e) pantothenic acid, to form a composition, wherein (i) the composition is substantially free of mobile bound water; (ii) the composition does not contain a hydrate form of any ingredient contained therein; (iii) the composition resists reactions that reduce potency of oxidizable vitamins; (iv) the composition reduces oxidation induced spotting of the tablet; and (v) the composition stabilizes disintegration behavior of the tablet.

5. A multivitamin and mineral supplement comprising about 15 to about 600 mg vitamin C; and about 20 IU to about 200 IU Vitamin E; about 0 to about 400 mg magnesium, about 0 to about 50 mg zinc, about 0 to about 12 mg manganese, about 0 to about 4 mg copper, about 0 to about 300 mcg chromium and about 0 to about 18 mg iron; and a therapeutically effective amount of niacin and pantothenic acid; and anhydrous dicalcium phosphate and further wherein (i) the supplement is substantially free of mobile bound water; (ii) the supplement does not contain a hydrate form of any ingredient contained therein; (iii) the supplement resists reactions that reduce the potency of oxidizable vitamins; (iv) the supplement reduces oxidation induced spotting of the tablet; and (v) the supplement stabilizes disintegration behavior of the tablet.

6. A method for preparing multivitamin and mineral tablets comprising: combining at least one polyvalent metal selected from the group consisting of iron, magnesium, zinc, selenium, copper, cobalt, manganese, molybdenum, vanadium, nickel, tin, chromium and combinations thereof, and at least one oxidizable vitamin selected from the group consisting of Vitamin C, Vitamin E, Vitamin A, Vitamin A precursors, Vitamin $B_6$, Vitamin $D_3$, folic acid and combinations thereof to form a composition, wherein (i) the composition is substantially free of mobile bound water; (ii) the composition does not contain a hydrate form of any ingredient contained therein; (iii) the composition resists reactions that reduce the potency of oxidizable vitamins; (iv) the composition reduces oxidation induced spotting of the tablet; and (v) the composition stabilizes disintegration behavior of the tablet.

* * * * *